(12) United States Patent
Zhang et al.

(10) Patent No.: US 9,934,668 B2
(45) Date of Patent: Apr. 3, 2018

(54) METHOD AND APPARATUS FOR IDENTIFYING TRANSITIONS BETWEEN SITTING AND STANDING POSTURES (71) Applicant: KONINKLIJKE PHILIPS N.V., Eindhoven (NL)

(72) Inventors: Wei Zhang, Eindhoven (NL); Fabian-Felix Wahle, Bergisch Gladbach (DE)

(73) Assignee: KONINKLIJKE N.V., Eindhoven (NL)

( * ) Notice: Subject to any disclaimer, the term of this patent is extended or adjusted under 35 U.S.C. 154(b) by 178 days.

(21) Appl. No.: 14/646,404

(22) PCT Filed: Nov. 29, 2013

(86) PCT No.: PCT/IB2013/060496
§ 371 (c)(1),
(2) Date: May 21, 2015

(87) PCT Pub. No.: WO2014/083538
PCT Pub. Date: Jun. 5, 2014

(65) Prior Publication Data
US 2015/0302720 A1    Oct. 22, 2015

Related U.S. Application Data (60) Provisional application No. 61/731,576, filed on Nov. 30, 2012.

(51) Int. Cl.
*G08B 23/00*     (2006.01)
*G08B 21/04*     (2006.01)
(Continued)

(52) U.S. Cl.
CPC ........ *G08B 21/0446* (2013.01); *A61B 5/1116* (2013.01); *A61B 5/725* (2013.01);
(Continued)

(58) Field of Classification Search
CPC .................................... G06F 1/00; G06T 1/00
See application file for complete search history.

(56) References Cited

U.S. PATENT DOCUMENTS

| 7,478,009 B2 | 1/2009 | Cabrera et al. |
| 8,206,325 B1 | 6/2012 | Najafi et al. |

(Continued)

FOREIGN PATENT DOCUMENTS

| CN | 101950464 A | 1/2011 |
| EP | 1302162 A2 | 4/2003 |

(Continued)

OTHER PUBLICATIONS

Adlerton et al: "Forceplate and Accelerometer Measures for Evalutatin the Effect of Muscle Fatigue on Postural Control During One-Legged Stance"; Physiotherapy RE Int. 2003:8(4),pp. 187-199.

(Continued)

*Primary Examiner* — Shirley Lu (57) ABSTRACT

There is provided a method for identifying transitions between a standing posture and a sitting posture by a user, the method comprising obtaining measurements of the acceleration experienced by the user during movement; obtaining a signal indicating the height of a part of the user during movement; processing the measurements of the acceleration to identify candidate movements corresponding to transitions between a standing posture and a sitting posture; and determining an identified candidate movement as a transition from a sitting posture to a standing posture where the identified candidate movement coincides with an increase in height in the signal and an identified candidate movement as a transition from a standing posture to a sitting posture where the identified candidate movement coincides with a decrease in height in the signal.

15 Claims, 6 Drawing Sheets

(51) Int. Cl.
*A61B 5/00* (2006.01)
*A61B 5/11* (2006.01)

(52) U.S. Cl.
CPC .......... *A61B 5/7246* (2013.01); *A61B 5/6822* (2013.01); *A61B 5/7282* (2013.01); *A61B 2562/0219* (2013.01)

(56) References Cited

U.S. PATENT DOCUMENTS

| | | | |
|---|---|---|---|
| 2004/0015103 A1* | 1/2004 | Aminian | A61B 5/1116 |
| | | | 600/595 |
| 2008/0275349 A1* | 11/2008 | Halperin | A61B 5/0205 |
| | | | 600/484 |
| 2011/0215925 A1 | 9/2011 | Chen et al. | |
| 2012/0013286 A1* | 1/2012 | Taniguchi | G01D 5/24476 |
| | | | 318/563 |
| 2012/0072168 A1* | 3/2012 | Yin | A61B 5/061 |
| | | | 702/150 |

FOREIGN PATENT DOCUMENTS

| | | |
|---|---|---|
| RU | 2385669 C2 | 4/2010 |
| WO | 2007021972 A2 | 2/2007 |
| WO | 2010035187 A1 | 4/2010 |
| WO | 2010126878 A1 | 11/2010 |
| WO | 2010134010 A1 | 11/2010 |
| WO | 2011055718 A1 | 5/2011 |
| WO | 2013001411 A1 | 1/2013 |
| WO | 2013030703 A1 | 3/2013 |

OTHER PUBLICATIONS

Adachi et al: "Development of Walking Analysis System Consisting of Mobile Force Plate and Motion Sensor"; Conf Proc IEEE Eng Med Biol Soc., 2011, pp. 4022-4025.

* cited by examiner

METHOD AND APPARATUS FOR IDENTIFYING TRANSITIONS BETWEEN SITTING AND STANDING POSTURES

CROSS-REFERENCE TO PRIOR APPLICATIONS

This application is the U.S. National Phase application under 35 U.S.C. § 371 of International Application No. PCT/IB2013/060496, filed on Nov. 29, 2013, which claims the benefit of U.S. Provisional Patent Application No. 61/731,576, filed on Nov. 30, 2012. These applications are hereby incorporated by reference in their entirety herein.

TECHNICAL FIELD OF THE INVENTION

The invention relates to a method and apparatus for identifying transitions between a sitting posture and a standing posture by a user from measurements of the movement of the user.

BACKGROUND TO THE INVENTION

Falls are one of the greatest health risk factors for elderly people. About one third of older people above the age of 65 fall at least once a year.

Many of these falls could be avoided by early identification of fall risk and the application of effective and targeted fall prevention programs. Fall prevention trials based on strength and balance training (SBT) have shown that the risk of falling for elderly people can be reduced.

An important parameter for the assessment of fall risk is the amount of daily activity. For frail elderly people, who are the largest part of the population with a high fall risk, the amount of time that they spend 'on legs' (i.e. walking, standing, etc.) over the course of a day provides a useful insight into their fall risk. The parameter "time-on-leg" corresponds to the amount of time that the person is performing particular weight-bearing activities or is in weight-bearing postures like regular/irregular walking, standing, etc. On the other hand, the parameter "time-off-leg" corresponds to the amount of time that the person spends doing non weight-bearing activities or being in non weight-bearing postures like lying, sitting, etc. Continuous or regular monitoring and analysis of "time-on-leg" for a particular person in daily life situations is complementary to standard physical tests for accurate and reliable fall risk assessment.

However, reliable assessment of daily activity or time-on-leg is difficult. The most commonly used approach is for the person themselves to log their activities. However, self-reporting comes with many drawbacks and generally produces unreliable and insufficient information for accurate assessment.

Although, recent development of on-body sensing technology provides objective measures of daily activity, many currently available products are only able to detect and monitor dynamic activities like running and regular walking, which is not particularly relevant when analyzing the daily life of the frail population. Some products do exist that provide analysis of postures, but they require the user to wear the sensors on inconvenient locations such as the thighs. To obtain good compliance in using the assessment tool, the sensor platform should ideally be located on the upper trunk in the form of a pendant-worn or similar device. However, it is difficult to detect postures such as sitting and standing from movement signals obtained using a device in this position.

Therefore, there is a need for a method and apparatus that can identify when a user has transitioned from a sitting posture to a standing posture and vice versa from measurements of the movement of the user. Identifying these posture changes allows an estimation of the time-on-leg for the user. The time-on-leg can be the sum of all time periods when the user is determined not to be sitting or lying down, e.g. following a transition from a sitting posture to a standing posture until the next transition from a standing posture to a sitting posture.

SUMMARY OF THE INVENTION

According to a first aspect of the invention, there is provided a method for identifying transitions between a standing posture and a sitting posture by a user, the method comprising obtaining measurements of the acceleration experienced by the user during movement; obtaining a signal indicating the height of a part of the user during movement; processing the measurements of the acceleration to identify candidate movements corresponding to transitions between a standing posture and a sitting posture; and determining an identified candidate movement as a transition from a sitting posture to a standing posture where the identified candidate movement coincides with an increase in height in the signal and an identified candidate movement as a transition from a standing posture to a sitting posture where the identified candidate movement coincides with a decrease in height in the signal.

In some embodiments, the step of obtaining a signal indicating the height comprises obtaining the signal by processing the output of an air pressure sensor that is attached to the user.

In alternative embodiments, the step of obtaining a signal indicating the height comprises obtaining the signal by processing the measurements of the acceleration experienced by the user during movement.

In some embodiments, the step of obtaining measurements of the vertical acceleration experienced by the user during movement comprises obtaining measurements of the acceleration in three-dimensions experienced by the user during movement; and processing the measurements of the acceleration to estimate the vertical acceleration experienced by the user.

In some embodiments, the step of processing the measurements comprises computing the norm of the measurements.

Preferably, the step of processing the measurements of the acceleration to identify candidate movements corresponding to transitions between a standing posture and a sitting posture comprises matching the measurements of the acceleration to a predetermined acceleration profile for a sit-to-stand transfer.

In preferred embodiments, the step of matching the measurements of the acceleration to a predetermined acceleration profile for a sit-to-stand transfer comprises filtering the measurements of acceleration with the predetermined acceleration profile to produce a forward-filtered signal; reversing the forward-filtered signal; and filtering the reversed signal with the predetermined acceleration profile.

Preferably, the step of processing the measurements of the acceleration further comprises filtering the signal resulting from the step of matching with a filter that enhances the magnitude of the parts of the signal that correspond to sit-to-stand and stand-to-sit transfers and that suppresses the magnitude of the parts of the signal that correspond to the user walking.

In some embodiments, the step of filtering comprises (a) for a subset of samples in a window on the signal resulting from the step of matching: (i) determining the average of the samples in the subset; (ii) subtracting the determined average from each of the samples in the subset; (iii) determining the absolute value of each sample in the output of step (ii); (iv) determining the average of the samples in the output of step (iii); (b) moving the window across the signal resulting from the step of matching and repeating step (a); and (c) determining the moving average of the signal obtained in step (b) to produce a filtered signal.

In alternative embodiments, the step of filtering comprises (a) for a subset of samples in a window on the signal resulting from the step of matching: (i) subtracting a value from each of the samples in the subset; (ii) determining the absolute value of each sample in the output of step (i); (iii) determining the average of the samples in the output of step (ii); (b) moving the window across the signal resulting from the step of matching and repeating step (a); and (c) determining the moving average of the signal obtained in step (b) to produce a filtered signal.

In some embodiments, the step of processing the measurements of the acceleration further comprises identifying candidate movements in the filtered signal as the peaks in the filtered signal. In these embodiments, a candidate movement is preferably identified where the peak has a magnitude greater than a threshold value.

The step of processing the measurements of the acceleration to identify candidate movements corresponding to transitions between a standing posture and a sitting posture can further comprise estimating the start and end times for each identified candidate movement as the times corresponding to the samples either side of the corresponding peak in the filtered signal where the magnitude of the samples are equal to a predetermined proportion of the threshold value.

In particular embodiments, the method further comprises the step of determining the change in height for each candidate movement from the obtained height signal by determining the height before the candidate movement as the average of the height of the part of the user over a window covering samples in the height signal before the estimated start time for the candidate movement; determining the height after the candidate movement as the average of the height of the part of the user over a window covering samples in the height signal after the estimated end time for the candidate movement; and subtracting the determined height before the candidate movement from the determined height before the candidate movement to give the change in height during the candidate movement.

According to a second aspect of the invention, there is provided a method of determining the time-on-leg for a user, the method comprising identifying transitions between a standing posture and a sitting posture by the user as described above; determining when the user is on their feet as the time periods following a transition from a sitting posture to a standing posture until the next transition from a standing posture to a sitting posture; and summing the duration of each of the time periods to give the time-on-leg.

According to a third aspect of the invention, there is provided a method of determining a risk of falling for a user, the method comprising determining the time-on-leg as described above; and determining a risk of falling for the user from the determined time-on-leg.

According to a fourth aspect of the invention, there is provided a computer program product, comprising computer program code that, when executed on a computer or processor, causes the computer or processor to identify transitions between a standing posture and a sitting posture in measurements of the movement of a user according to any of the methods described above.

According to a fifth aspect of the invention, there is provided an apparatus for identifying transitions between a standing posture and a sitting posture in measurements of the movement of a user, the apparatus comprising a processing unit configured to process measurements of the acceleration experienced by the user to identify candidate movements corresponding to transitions between a standing posture and a sitting posture; and determine an identified candidate movement as a transition from a sitting posture to a standing posture where the identified candidate movement coincides with an increase in height in a signal indicating the height of a part of the user during movement, and determine an identified candidate movement as a transition from a standing posture to a sitting posture where the identified candidate movement coincides with a decrease in height in the signal indicating the height of the part of the user.

Various other embodiments of the apparatus are also contemplated in which the processing unit is further configured to execute any of the above-described method steps.

According to a sixth aspect of the invention, there is provided a device that is configured to be worn by a user, the device comprising an accelerometer that measures the acceleration acting on the device in three dimensions; and an apparatus as described above, wherein the processing unit is configured to process the measurements of the acceleration from the accelerometer.

According to a seventh aspect of the invention, there is provided a system that comprises a device that is configured to be worn by a user, the device comprising an accelerometer that measures the acceleration acting on the device in three-dimensions; and a base unit that is configured to communicate with the device, and that comprises an apparatus as described above, wherein the processing unit is configured to process the measurements of the acceleration from the accelerometer.

BRIEF DESCRIPTION OF THE DRAWINGS

Embodiments of the invention will now be described, by way of example only, with reference to the following drawings, in which.

DETAILED DESCRIPTION OF THE PREFERRED EMBODIMENTS

Figure 1:
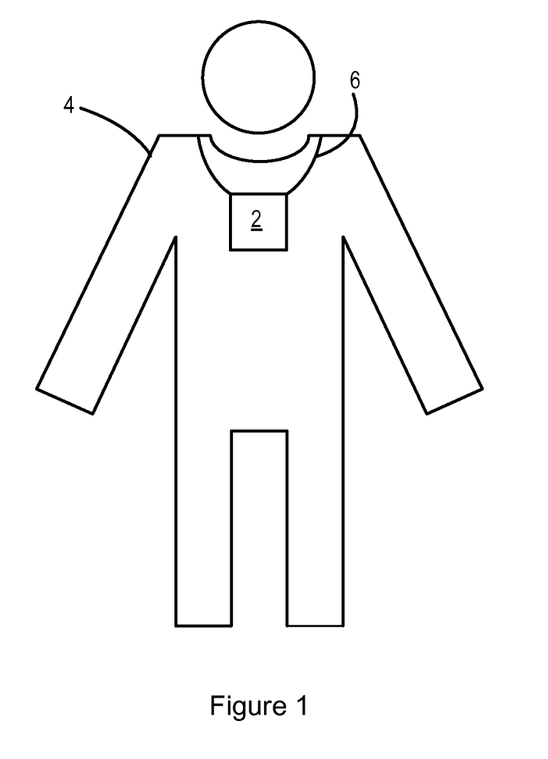
FIG. 1 shows a sensor unit in accordance with an embodiment of the invention attached to a user.

As shown in FIG. 1, the invention provides an apparatus in the form of a sensor unit 2 that is to be worn by the user 4. In the illustrated embodiment, the sensor unit 2 is provided in the form of a pendant with a neck cord 6 for placement around the user's neck. Alternatively, the sensor unit 2 can be configured to be worn at or on a different part of the user's body, such as the trunk, pelvis or sternum, and will comprise a suitable arrangement for attaching the sensor unit 2 to that part of the body (for example a belt or a strap if the unit 2 is attached to the pelvis or sternum).

The sensor unit 2 is used to measure the movement of the user 4 and to process the measurements to determine when the user 4 has executed a change in posture from a sitting posture to a standing posture (also referred to herein as a "sit-to-stand transfer") and from a standing posture to a sitting posture (also referred to herein as a "stand-to-sit transfer"). As used herein, a "standing" posture corresponds to any posture in which the user is on their feet (i.e. performing a weight-bearing activity), and includes walking/running as well as standing still. Thus, the sensor unit 2 can be used to process the measurements to determine when the user 4 has executed a simple sit-to-standing upright posture change as well as a change from a sitting posture to walking (and vice versa). In some embodiments, the sensor unit 2 is also used to determine the time-on-leg for the user from the measurements of the movement of the body of the user 4, and optionally also an indication of the fall risk for the user 4 from the determined time-on-leg.

In alternative implementations, some or all of the processing of the measurements, determination of the time-on-leg and the indication of the fall risk can be performed in a base unit that is separate to the sensor unit 2 worn by the user 4 (not shown in FIG. 1). In this case, the sensor unit 2 can transmit the movement measurements or information on the identified posture changes to the base unit using a wired or wireless connection.

Figure 2:
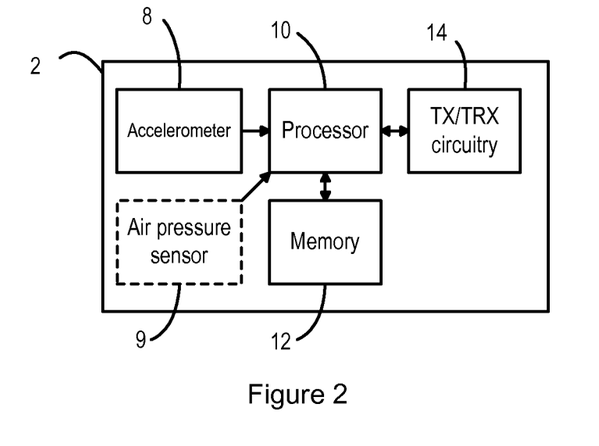
FIG. 2 is a block diagram of a sensor unit in accordance with an embodiment of the invention.

FIG. 2 shows an embodiment of the sensor unit 2 in accordance with the invention. The sensor unit 2 comprises an accelerometer 8 that measures acceleration along three orthogonal axes (and that outputs respective signals indicating the acceleration along each of the axes) and an optional sensor 9 that measures the altitude or height of the sensor unit 2 above the ground (or more particularly that measures changes in the altitude or height of the sensor unit 2 above the ground, or enables those changes to be measured). The sensor 9 for measuring the altitude or height of the sensor unit 2 can comprise, for example, an altimeter or air pressure sensor, although those skilled in the art will be aware of other types of sensors that can be used. In some embodiments, the measurements from the accelerometer 8 can be processed to determine the height of the sensor unit 2 above the ground, or to determine the change in height of the sensor unit 2. The signals output by the accelerometer 8 and sensor 9 (where present) are provided to a processor 10 for analysis.

The sensor unit 2 also comprises a memory 12 and transmitter or transceiver circuitry 14. The memory 12 is used for storing measurements from the accelerometer 8 and sensor 9, and for storing the results of the analysis by the processor 10. The transmitter or transceiver circuitry 14 can be used for transmitting the results of the analysis to a remote (base) unit or a computer where they can be viewed or studied by the user or a healthcare provider.

In some embodiments, the accelerometer 8 is a microelectromechanical system (MEMS) accelerometer. The acceleration experienced by the accelerometer 8 can be sampled at a rate of 50 Hz, although it will be appreciated that many other sampling frequencies can be used. Where sensor 9 is an air pressure sensor or altimeter, the measurements of the height of the sensor unit 2 above the ground can be sampled at a frequency of around 1.8 Hz, although again it will be appreciated that other sampling frequencies can be used.

Depending on the particular type of sensor used for the sensor 9 for measuring height, the sensor 9 may output signals indicative of the height above the ground (or sea level in the case of an air pressure sensor), in which case the time series of height measurements can be analyzed by the processor 10 to determine the change in height from one measurement sample to the next (or over a predetermined number of measurement samples). Alternatively, the sensor 9 can directly output an indication of the change in height of the sensor unit 2 from the previous or an earlier specified measurement sample.

In an embodiment of the invention, the measurements collected by the accelerometer 8 and sensor 9 are analyzed by the processor 10 in the sensor device 2 to determine the occurrence of sit-to-stand and stand-to-sit transfers, and optionally the time-on-leg and a fall risk. Alternatively, the measurements from the accelerometer 8 and sensor 9 could be transmitted to a base unit via the transmitter/transceiver circuitry 14, with the base unit analyzing the measurements to determine the occurrence of sit-to-stand and stand-to-sit transfers. In either case, the processing can be performed in (near) real-time or the measurements from the accelerometer 8 and the sensor 9 can be stored in the memory 12 or the base unit for future processing (i.e. offline).

Figure 3:
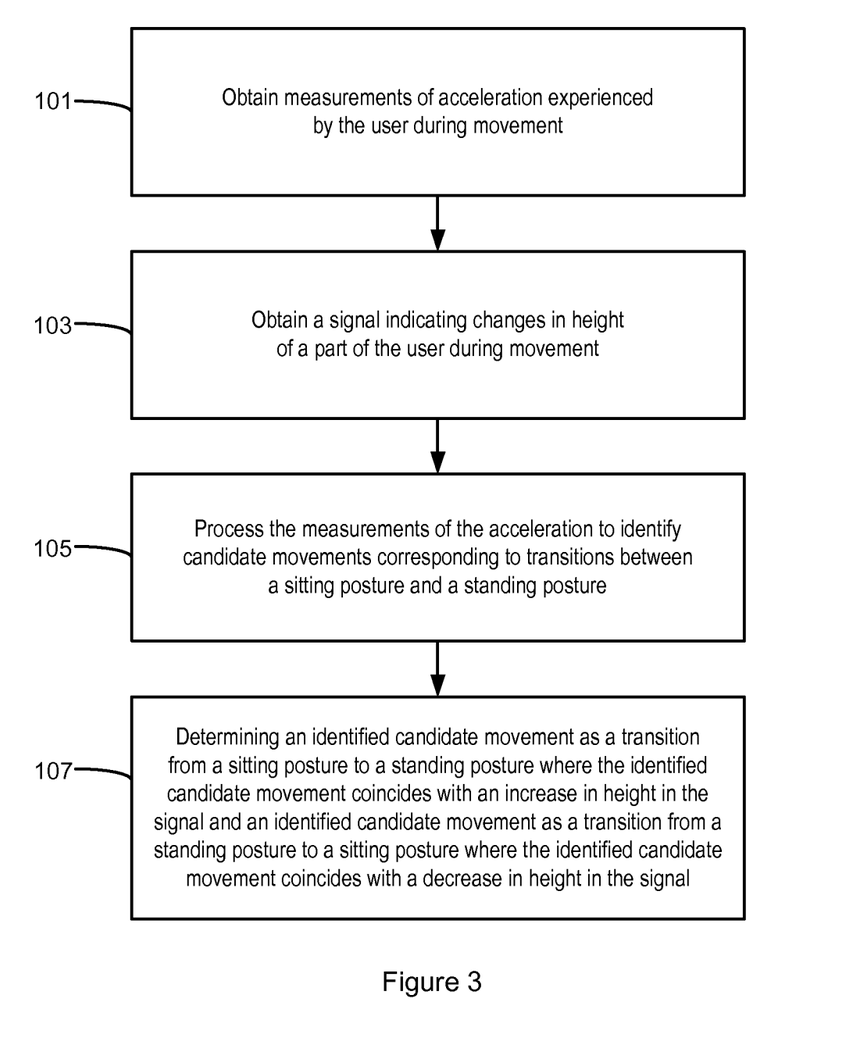
FIG. 3 is a flowchart illustrating a method for identifying posture transitions from measurements of the movement of a user.

FIG. 3 shows a flowchart illustrating the steps required to identify transitions between a sitting posture and an upright posture (so e.g. standing or walking) in measurements of the movement of the user. Firstly (step 101), measurements of the acceleration experienced by the sensor unit 2 (and therefore the user 4, since the user is wearing the sensor unit 2) are obtained. Secondly (step 103), a signal indicating changes in height of a part of the user is obtained. As noted above, this signal can be obtained from an air pressure or altitude sensor, or it can be obtained by processing the measurements of the acceleration to determine absolute height or changes in height of the user.

The measurements of the acceleration and height (or changes in height) in steps 101 and 103 are obtained over substantially the same period of time.

Next, in step 105, the measurements of the acceleration are processed to identify movements in the measurements that may correspond to sit-to-stand transfers and stand-to-sit transfers by the user 4. The parts of the accelerometer measurement (i.e. a sequence of measurement samples) that are identified in this step as possibly corresponding to sit-to-stand and stand-to-sit transfers are termed 'candidate movements'.

In a preferred embodiment of the invention, as described in more detail below, the candidate movements are identified by matching the measurements of the acceleration to an acceleration profile that is expected to occur during a sit-to-stand transfer.

Figure 4:
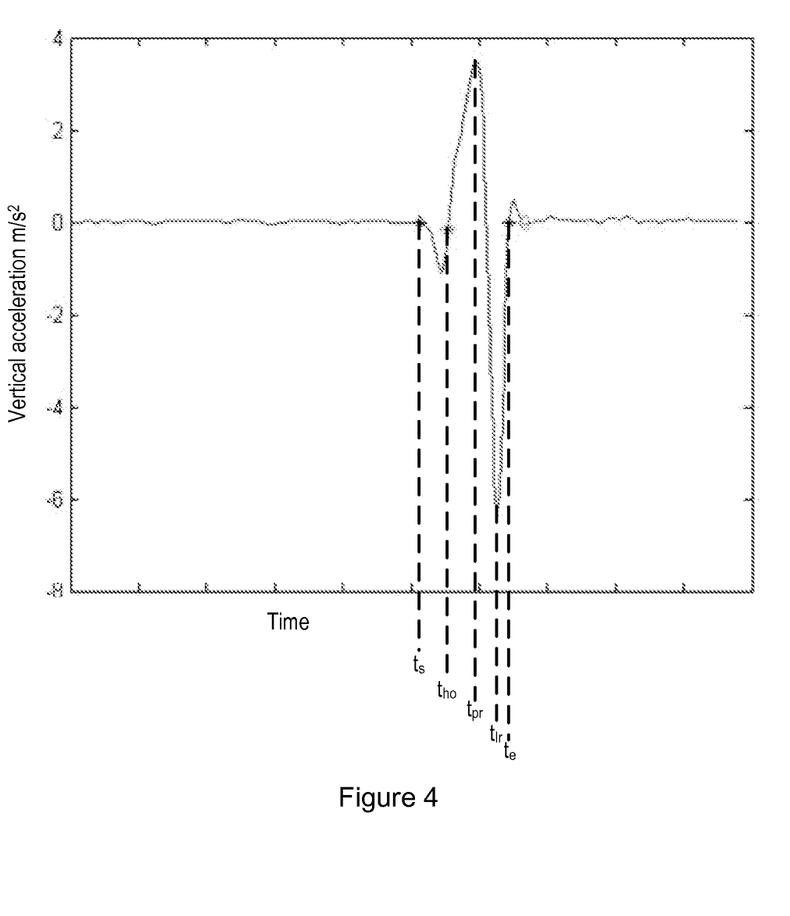
FIG. 4 is a graph illustrating an example of the variation in vertical acceleration during a sit-to-stand transfer.

The graph in FIG. 4 shows the acceleration measured in the vertical direction during a typical sit-to-stand motion. The user 4 starts from rest (i.e. the measured acceleration in the vertical direction is approximately 0) and the user begins to move at time $t_s$. The acceleration measured at this time is denoted $Acc_{vert\_s}$. There is typically a small minimum in the acceleration profile just after the user starts to move and before they rise off their chair. Subsequently, the user's hip leaves the means of support (i.e. chair) at time $t_{ho}$ ('ho' represents hip off), and the acceleration at this time is denoted $Acc_{vert\_ho}$. The acceleration in the vertical direction then increases to a peak (the peak reaction) denoted $Acc_{vert\_pr}$ at time $t_{pr}$. The peak reaction is followed by the lowest reaction which is a negative acceleration denoted $Acc_{vert\_lr}$ occurring at time $t_{lr}$. The end of the movement occurs at time $t_e$, with the acceleration denoted $Acc_{vert\_e}$.

Thus, in step 105 of the flowchart in FIG. 3, the candidate movements are identified by analyzing the accelerometer measurements to identify sequences of samples whose profile match or substantially match the profile shown in FIG. 4.

In step 107, the change in height occurring during or around the time of each candidate movement is determined from the measurements obtained in step 103 and used to classify the candidate movements as a sit-to-stand or stand-to-sit transfer. In particular, the altitude before and after the candidate movement is analyzed to determine the height change. In some embodiments, the mean or median value of the altitude in a window (e.g. of 1 second length) before and after the candidate movement can be determined and the difference found. Then, a candidate movement is identified as a sit-to-stand transfer when it occurs at the same time (or sufficiently close in time) to an increase in height, and a candidate movement is identified as a stand-to-sit transfer when it occurs at the same time (or sufficiently close in time) to a decrease in height. In some embodiments, to classify a candidate movement as a sit-to-stand or stand-to-sit transfer, the increase or decrease in height must be within a predetermined range. The predetermined range encompasses the height changes expected to occur during or around a typical sit-to-stand transfer and stand-to-sit transfer, which for example can correspond generally to length of the user's thigh. In this case, the lower bound for the range can be around 0.1 or 0.2 meters, for example, and the upper bound for the range can be set to a value of 0.6, 0.75, 0.8 or 1 meter, for example. It will be appreciated that the threshold can be personalized to the height or thigh length of the user and can also be set taking into account the resolution of the height or altitude measurements provided by the sensor 9.

It will also be appreciated that sit-to-stand and stand-to-sit transfers can alternatively be determined by comparing the change in height to a threshold value, with transfers being identified where the change in height exceeds the threshold value. In this case, the threshold can correspond to the lower bound for the predetermined range described above. However, this embodiment may result in a higher false positive identification rate than the range embodiment described above, since activities such as climbing or descending the stairs may be identified as a sit-to-stand or stand-to-sit transfer (whereas this movement would be discarded as a possible sit-to-stand or stand-to-sit transfer by the upper bound of 0.6-1 meter in the range embodiment).

Figure 5:
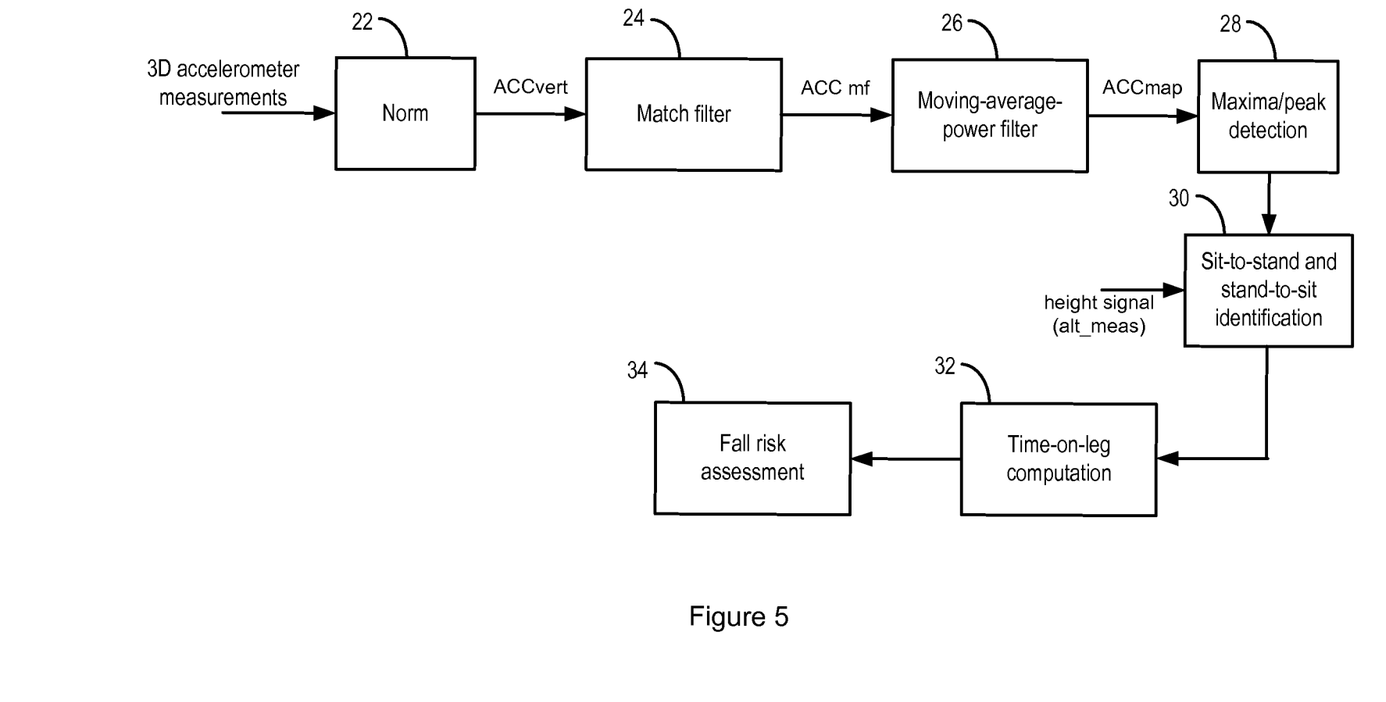
FIG. 5 is a block diagram illustrating an algorithm for detecting sit-to-stand and stand-to-sit transfers.

An algorithm illustrating the detection of sit-to-stand and stand-to-sit transfers in accordance with a specific embodiment of the invention is shown in FIG. 5. The algorithm takes as an input the three-dimensional acceleration signal measured by the accelerometer 8 (which comprises a separate signal for each of the three axes of the accelerometer 8) and a signal indicating the change in height of the sensor unit 2/user 4 over time. As noted above, the signal indicating the change in height of the sensor unit 2/user 4 can be obtained using an air pressure or altitude sensor 9, or it can be estimated from the acceleration signal (for example by double integrating the vertical component of acceleration to give height or a change in height).

For completeness, an exemplary technique for processing a signal from an air pressure in order to obtain a height change signal is described below.

Firstly, a raw air pressure signal $p_t$ is obtained from the air pressure sensor 9. As mentioned previously, the air pressure can be sampled at a rate of 1.8 Hz (or in any case at a much lower sampling rate than the acceleration signals). Therefore, the air pressure signal $p_t$ is firstly upsampled to match the sampling rate (e.g. 50 Hz) of the acceleration signals (the upsampled pressure signal is denoted $p_t'$). The altitude at time t (denoted alt_t) can then be estimated from the air pressure sensor measurements using equation 1 below:

$$\text{alt}\_t = 44330*(1-p_t'/101325)^{0.19} \quad (1)$$

Equation (1) is derived from the air pressure to altitude conversion function shown in equation (2):

$$\text{alt}\_t = \frac{T_0}{L}\left(1 - \left(\frac{p}{p_0}\right)^{\frac{RL}{gM}}\right) \quad (2)$$

where:

| Symbol | Quantity | Typical Value |
|---|---|---|
| alt_t | Altitude in meters | |
| p | Air pressure | |
| $p_0$ | Standard atmospheric pressure at sea level | 101325 kPa |
| L | Temperature lapse rate | 0.0065 Km$^{-1}$ |
| $T_0$ | Standard temperature at sea level | 288.15 K |
| G | Gravitational acceleration at Earth's surface | 9.80665 ms$^{-2}$ |
| M | Molar mass of dry air | 0.0289644 kg mol$^{-1}$ |
| R | Universal gas constant | 8.31447 J mol$^{-1}$ K$^{-1}$ |

Figure 6:
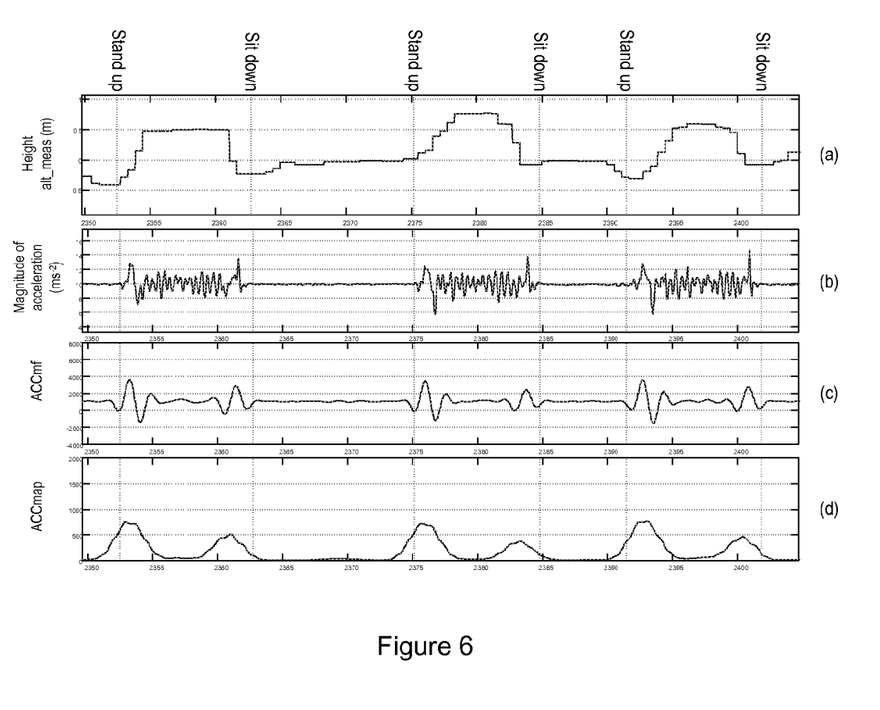
FIG. 6 is a set of graphs showing signals at various stages of the processing algorithm in FIG. 5.

The resulting altitude signal is then smoothed, for example with a median or moving average filter having a predetermined length, for example of around 3 seconds, or a Butterworth low-pass filter. In preferred implementations, a $2^{nd}$ order Butterworth filter with a 2 Hz cut-off frequency can be used as this allows the trajectory of a transition conducted by the user to be well obtained (although it requires the air pressure sensor to operate with a higher sampling frequency, e.g. 10 Hz or greater). The filter is applied to the time series of estimated altitudes, resulting in a smoothed altitude signal alt_meas which is shown in FIG. 6(*a*).

It will be appreciated that in alternative embodiments of the invention where a different type of altitude, height or change in height sensor is used, the above processing can be adapted or omitted accordingly.

Also, although not shown in FIG. 5, the measurements of the acceleration from the accelerometer 8 (i.e. three signals representing the acceleration measured along a respective axis of the 3D accelerometer 8) can be pre-processed prior to input to the main processing stages according to the invention. For example, the three signals can be low-pass filtered to remove noise which could affect the accuracy of the subsequent processing. In some cases, a Butterworth low-pass filter with a cut-off frequency of 2 Hz is applied to the signals from each of the three axes of the accelerometer 8. Alternatively, different filter characteristics such as a Chebyshev low-pass filter or other types of filter known to those skilled in the art can be applied. It will also be appreciated that the cut-off frequency of 2 Hz could be varied dependent on the particular characteristics of the noise from the accelerometer 8.

At the start of the algorithm shown in FIG. 5, the measurements from the 3D accelerometer (or the filtered measurements described above) are processed to estimate the vertical acceleration. In preferred embodiments, the estimate of the vertical acceleration is determined by taking the norm of the 3D acceleration signal. The computation of the vertical acceleration is required because when the sensor unit 2 is in the form of a pendant, it is able to freely move at the chest location. Therefore, in preferred embodiments, the 3D accelerometer signal (or the filtered measurements described above) are input to a norm computation block 22. The norm computation block 22 computes the norm for each sample in the 3D acceleration signal, i.e.

$$ACCvert(i) = \sqrt{(ACC_x(i)^2 + ACC_y(i)^2 + ACC_z(i)^2)} \qquad (3)$$

where $ACC_x(i)$, $ACC_y(i)$ and $ACC_z(i)$ are the components of acceleration along the x, y and z axes of the accelerometer 8 respectively for the i-th sample.

It will be appreciated that in alternative embodiments other ways of determining the vertical acceleration from the 3D acceleration signal can be used.

FIG. 6(b) shows an exemplary signal representing the norm of a 3D acceleration signal obtained from measurements by a sensor unit 2 for a user 4 that performed a sit-to-stand transfer (labeled 'stand up' in FIG. 6), walking for 3 meters and then sitting back down (labeled 'sit down' in FIG. 6), which was repeated three times. It can be seen in FIG. 6(b) that there are three separate areas of activity represented in the signal.

The normed acceleration signal (or estimate of vertical acceleration obtained by other techniques), ACCvert, is input to a filter block 24 that matches the ACCvert signal to a predetermined pattern representing the acceleration that is expected to occur during a sit-to-stand transfer.

In a preferred embodiment, block 24 applies a matched filter having an impulse response that approximates the acceleration experienced during a sit-to-stand transfer to the vertical acceleration signal (ACCvert) output from the norm computation block 22. To identify both sit-to-stand and stand-to-sit transfers using this matched filter, the signal in FIG. 6(b) will first be filtered using the matched filter in forward direction. Then the filtered signal is reversed and filtered again using the matched filter to produce the signal in FIG. 6(c). The filtered signal is denoted ACCmf and is shown in FIG. 6(c). ACCmf preserves the pattern in the signal which matches to the template illustrated in FIG. 7 while suppresses those do not match. The output of the matched filter 24 is a set of coefficients that indicate the match of the measurements to the pattern. Each coefficient represents the match of a number of consecutive measurement samples (covering a time period of the same length as the predetermined pattern) to the predetermined pattern. The higher the coefficient, the better the match of the measurements to the pattern (and therefore the greater the chance that a sit-to-stand transfer or stand-to-sit transfer has occurred).

Figure 7:
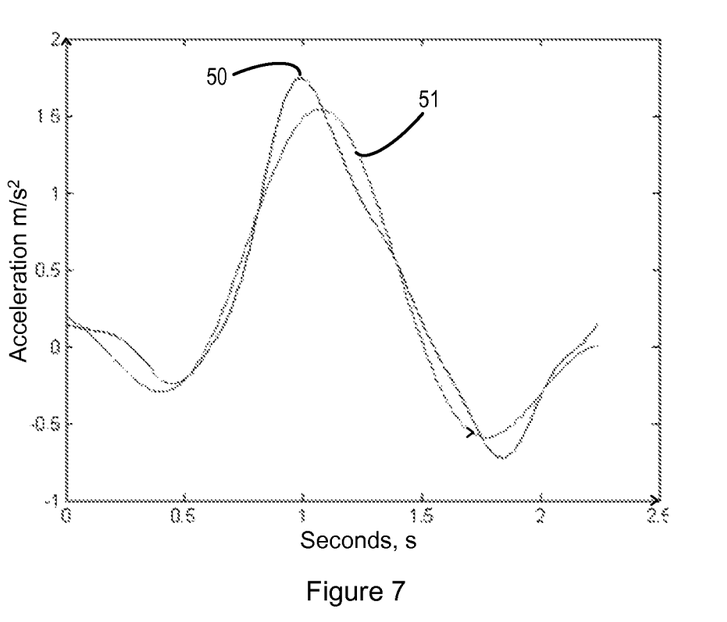
FIG. 7 illustrates an exemplary matched filter which has been optimized for use in detecting a sit-to-stand transfer.

In a preferred embodiment, the matched filter used in block 24 can be as shown in FIG. 7, which has been optimized to detect a sit-to-stand transfer. The matched filter shown in FIG. 7 excludes gravity (9.8 ms$^{-2}$). The first curve 50 shows a typical vertical acceleration pattern of a sit-to-stand transfer. The second curve 51 shows an applied matched filter characteristic that approximates the first curve 50. It will be appreciated that the matched filter characteristic may be expressed using many different functions, but in this embodiment, the matched filter characteristic is given by equation 4 below.

$$A_1 \cdot \mathrm{sinc}[W_1(t-t_1)] + A_2 \cdot \mathrm{sinc}[W_2(t-t_2)] \qquad (4)$$

This characteristic is a combination of two sinc functions with scale parameters defined in p. p is a parameter vector with six elements:

$$[A_1, A_2, W_1, W_2, t_1, t_2] \qquad (5)$$

Each entry in p defines a different scale parameter. $A_1$ and $A_2$ are amplitude scale parameters, which define the peak deviation of the two sinc waves respectively. The parameters $W_1$ and $W_2$ are frequency scale parameters, which define the frequency of the two sinc waves. The parameters $t_1$ and $t_2$ are phase scale parameters, which define the position of the sinc waves. The values of the six elements in the parameter vector p are set to tune the function of the matched filter to the sit-to-stand transfer characteristic 50 in FIG. 7.

It will be appreciated that the values of the elements of the parameter vector p can be provided by many known curve-fitting methods. In one case, the desired parameters could be calculated by applying a nonlinear least-squares regression algorithm, however many other types of fitting algorithms are well known in the art and could be applied. The nonlinear least-squares regression algorithm generates different parameter combinations corresponding to different functions. The generated functions are then fitted to the data set of desired patterns according to a least-squared error criterion. When the function yields a minimum value of least square error among the combination of parameters, an optimized fit has been found.

After match filtering, the match filtered signal (ACCmf) output by block 24 is passed through another filter block 26 that filters the ACCmf signal to enhance the parts of the signal that correspond to sit-to-stand and stand-to-sit transfers and to suppress the magnitude of the parts of the signal corresponding to the user walking.

In a preferred embodiment, the filter block 26 applies a moving average power filter to the ACCmf signal. In some implementations, the moving average power filter 26 operates according to the following function:

```
sigOut(i)=mean{abs[sigIn(i:i+wSz−1)−
    mean(sigIn(i:i+wSz−1))]};
sigOut = MA(sigOut);
``` sigIn is a subset of samples in the match filtered acceleration signal (ACCmf) in a window of predetermined length, for example 0.75 seconds (although other window sizes can be used), and wSz is the number of samples in the sliding window. The length of the window used by the moving average function may be the same length as the window used to select the input samples (sigIn), e.g. 0.75 seconds, but it may alternatively be different.

Thus, according to this function, a windowed subset of samples is identified in the ACCmf signal (sigIn) and (i) the mean of the samples in the subset is determined, (ii) the mean is subtracted from the each of the samples in the subset, (iii) the absolute value of each sample in the output of (ii) is determined, and (iv) the mean of the samples in the output of (iii) is determined. The window is moved across the ACCmf signal (for example one sample at a time, although for reduced computational load larger window steps can be used) and the above steps performed at each window position. The output signal formed from sliding the window across the ACCmf signal and performing the steps above is then processed (smoothed) using a moving average filter.

sigOut (or ACCmap as shown in FIGS. 5 and 6) is the output of the moving average power filter 26, and an exemplary signal is shown in FIG. 6(d). Thus, it can be seen that the signal is characterized by a number of peaks, each generally coinciding with a stand up or sit down transition by the user.

In alternative implementations, the moving average power filter 26 can operate according to the following function:

$$sigOut(i)=median\{abs[sigIn(i:i+wSz-1)-median(sigIn(i:i+wSz-1))]\};$$
$$sigOut = MA(sigOut);$$

or $$sigOut(i)=median\{abs[sigIn(i:i+wSz-1)-Thres]\};$$
$$sigOut = MA(sigOut);$$

where Thres is a defined threshold based on, e.g. an estimate of gravity, of the mean or median value of all of the samples of sigIn. In the latter implementation, the filter 26 determines the difference between the sigIn value in the sliding window to a reference value. The reference value can be estimation of the mean or median of a subset (or the complete) signal, or a predefined reference value.

After the moving average power filtering in block 26, the filtered signal ACCmap is processed to identify candidate movements that might correspond to a sit-to-stand or stand-to-sit transfer by the user. The processing consists of firstly identifying any peak or maxima in the ACCmap signal in block 28. Preferably, only peaks having a magnitude above a peak threshold value are detected in the ACCmap signal. In the exemplary signal shown in FIG. 6(d), six peaks can be seen that will be identified by block 28 as candidate sit-to-stand or stand-to-sit transfers. For each identified peak (corresponding to a candidate transfer), an estimation of the time of the transfer is also determined. Preferably, this estimation is made by identifying the sample either side of the peak where the magnitude of ACCmap falls below a proportion of the peak threshold value (e.g. 50% of the peak threshold). The times corresponding to those samples provide the estimation of the start and end times of the transfer. The output of block 28 is an indication of the times at which maxima or peaks occur in the moving average power filtered signal.

It will be appreciated that the processing operations performed by the norm computation block 22, match filter block 24, moving average power filter block 26 and maxima/peak detection block 28 correspond generally to step 105 in FIG. 3.

As described above with reference to step 107 of FIG. 3, candidate sit-to-stand and stand-to-sit transfers corresponding to the peaks identified in block 28 are classified as sit-to-stand transfers when they occur at or around the same time as an increase in height of the sensor unit 2 and stand-to-sit transfers are classified as sit-to-stand transfers when they occur at or around the same time as a decrease in height of the sensor unit 2.

Thus, block 30 determines the change in height or altitude that has occurred at or around the time of each identified candidate sit-to-stand or stand-to-sit transfer. In addition to receiving the indication of the timing of the identified peaks from the peak detection block 28, the classification block 30 also receives the estimated altitude or height measurement signal, alt_meas.

For each identified peak, the classification block 30 determines the height change occurring within a predetermined time period of the peak using the height measurement signal, alt_meas. Thus, in some embodiments the classification block 30 applies a window of predetermined length to the height measurement signal alt_meas around the time that the particular identified peak occurs, and determines the height change that occurs across that window (e.g. by subtracting the height at the end of the window from the height at the start of the window, although those skilled in the art will be aware of other ways of determining the height change within a window on a signal). For example, in some alternative implementations, the mean or median value of the altitude in a window (e.g. of 1 second length) before and after the candidate movement can be determined and the difference found. In either implementation, the window may have a length of, for example, 1 second, but other lengths are possible.

If it is determined that there is an increase in height around the time that an identified peak occurs, then the classification block 30 classifies that peak as a sit-to-stand transfer. In alternative embodiments, the classification block 30 may require the increase in height to be greater than a threshold value (e.g. 0.1 meters) or within a predetermined range (e.g. 0.1 meters to 0.75 meters) in order to classify the peak as a sit-to-stand transfer.

Likewise, if it is determined that there is a decrease in height around the time that an identified peak occurs, then the classification block 30 classifies that peak as a stand-to-sit transfer. In alternative embodiments, the classification block 30 may require the (magnitude of the) decrease in height to be greater than a threshold value (e.g. 0.1 meters) or within a predetermined range (e.g. 0.1 meters to 0.75 meters) in order to classify the peak as a stand-to-sit transfer.

It will be appreciated that in embodiments where a threshold or predetermined range is applied to the height change, the value of the threshold or predetermined range can be determined based on the characteristics of the user, e.g. height or leg length.

The output of classification block 30 is an indication of the time or times at which sit-to-stand transfers have occurred and the time or times at which stand-to-sit transfers have occurred. These indications are used by 'time-on-leg' computation block 32 to determine the 'time-on-leg' for the user 4.

The computation block 32 determines the time that has elapsed from each sit-to-stand transfer to the following stand-to-sit transfer, and sums each elapsed time to determine the time-on-leg. The time-on-leg can be the sum of all time periods when the user is determined not to be sitting or lying down, e.g. following a transition from a sitting posture to a standing posture until the next transition from a standing posture to a sitting posture. In other words, the computation block 32 determines when the user is on their feet from the identified transfers, and determines the length of this time period.

The determined time-on-leg can be provided to a fall risk assessment block 34 that determines a fall risk for the user 4. In a simple case, the fall risk can be directly related to the determined time-on-leg (for example low values of time-on-leg can be associated with high fall risk, and vice versa), but in other cases the fall risk can be determined based on the time-on-leg and other fall-related parameters, such as those related to the stability of the gait of the user or the power used in completing a sit-to-stand transfer.

In addition to determining the time-on-leg from detected sit-to-stand and stand-to-sit transitions, other movements that can be detected from a 3D acceleration signal and/or a height signal, such as walking, etc., can be used to confirm that the user is in fact on their feet following a detected sit-to-stand transfer, and vice versa. For example, the variance of the acceleration signal can be used as an indication of movement. If the variance of the acceleration is above a threshold, it is likely that the user is moving around (and therefore likely to be on their feet). Those skilled in the art will be aware of other features that could be extracted from the acceleration signals to assist in verifying whether the user is on their feet or sat down.

In addition, those skilled in the art will appreciate that such features could be used by the classification block 30 in addition to the height signal to determine whether an identified candidate movement is a sit-to-stand or stand-to-sit transfer. Furthermore, those skilled in the art will appreciate that in embodiments that are alternative to the threshold-based classification technique described above, the classification block 30 may make use of different linear or non-linear classification techniques.

It will be appreciated that, in addition to determining the occurrence of sit-to-stand and stand-to-sit transfers for the purpose of determining the time-on-leg, the detection of one or both types of transfer can be used as part of a processing algorithm that assesses the performance of such transfers, for example including assessing the power generated by the user in performing the sit-to-stand transfer.

There is therefore provided a method and apparatus that can identify sit-to-stand and stand-to-sit transfers from measurements of the movement of a user. The identification of these transfers subsequently allows the time that the user spends on their feet to be reliably determined without requiring the user to manually record their activities, and also allows the fall risk of the user to be automatically assessed.

While the invention has been illustrated and described in detail in the drawings and foregoing description, such illustration and description are to be considered illustrative or exemplary and not restrictive; the invention is not limited to the disclosed embodiments.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A method for identifying transitions between a standing posture and a sitting posture by a user, the method comprising:

measuring, with an accelerometer, an acceleration experienced by the user during movement and outputting measurements of the acceleration;

measuring, with a sensor, a height of a part of the user during movement and outputting a signal indicating the height;

processing, with a hardware processor, the measurements of the acceleration to identify candidate movements corresponding to transitions between a standing posture and a sitting posture; and determining, with the hardware processor, an identified candidate movement as a transition from a sitting posture to a standing posture where the identified candidate movement coincides with an increase in the height in the signal and an identified candidate movement as a transition from a standing posture to a sitting posture where the identified candidate movement coincides with a decrease in the height in the signal.

2. The method as claimed in claim 1, wherein the step of processing the measurements of the acceleration to identify candidate movements corresponding to transitions between a standing posture and a sitting posture comprises matching the measurements of the acceleration to a predetermined acceleration profile for a sit-to-stand transfer.

3. The method as claimed in claim 2, wherein the step of matching the measurements of the acceleration to a predetermined acceleration profile for a sit-to-stand transfer comprises:

filtering the measurements of acceleration with the predetermined acceleration profile to produce a forward-filtered signal;

reversing the forward-filtered signal; and filtering the reversed signal with the predetermined acceleration profile.

4. The method as claimed in claim 2, wherein the step of processing the measurements of the acceleration further comprises filtering the signal resulting from the step of matching with a filter that enhances the magnitude of the parts of the signal that correspond to sit-to-stand and stand-to-sit transfers and that suppresses the magnitude of the parts of the signal that correspond to the user walking.

5. The method as claimed in claim 4, wherein the step of filtering comprises:

(a) for a subset of samples in a window on the signal resulting from the step of matching:
  (i) determining the average of the samples in the subset;
  (ii) subtracting the determined average from each of the samples in the subset;
  (iii) determining the absolute value of each sample in the output of step (ii);
  (iv) determining the average of the samples in the output of step (iii);

(b) moving the window across the signal resulting from the step of matching and repeating step (a);

(c) determining the moving average of the signal obtained in step (b) to produce a filtered signal;

or wherein the step of filtering comprises:

(a) for a subset of samples in a window on the signal resulting from the step of matching:
  (i) subtracting a value from each of the samples in the subset;
  (ii) determining the absolute value of each sample in the output of step (i);
  (iii) determining the average of the samples in the output of step (ii);

(b) moving the window across the signal resulting from the step of matching and repeating step (a); and (c) determining the moving average of the signal obtained in step (b) to produce a filtered signal.

6. The method as claimed in claim 4, wherein the step of processing the measurements of the acceleration further comprises:
identifying candidate movements in the filtered signal as the peaks in the filtered signal.

7. The method as claimed in claim 6, wherein a candidate movement is identified where the peak has a magnitude greater than a threshold value.

8. The method as claimed in claim 7, wherein the step of processing the measurements of the acceleration to identify candidate movements corresponding to transitions between a standing posture and a sitting posture further comprises:
estimating the start and end times for each identified candidate movement as the times corresponding to the samples either side of the corresponding peak in the filtered signal where the magnitude of the samples are equal to a predetermined proportion of the threshold value.

9. The method as claimed in claim 8, further comprising the step of determining the change in height for each candidate movement from the obtained height signal by:
determining the height before the candidate movement as the average of the height of the part of the user over a window covering samples in the height signal before the estimated start time for the candidate movement;
determining the height after the candidate movement as the average of the height of the part of the user over a window covering samples in the height signal after the estimated end time for the candidate movement; and
subtracting the determined height before the candidate movement from the determined height before the candidate movement to give the change in height during the candidate movement.

10. The method as claimed in claim 8, further comprising:
determining when the user is on their feet as the time periods following a transition from a sitting posture to a standing posture until the next transition from a standing posture to a sitting posture; and
summing the duration of each of the time periods to give the time-on-leg.

11. The method according to claim 10, the method further comprising:
determining a risk of falling for the user from the determined time-on-leg.

12. A non-transitory computer readable medium, comprising computer program code that, when executed on a computer, causes the computer to identify transitions between a standing posture and a sitting posture in measurements of the movement of a user by:

obtaining measurements of an acceleration experienced by the user during movement;
obtaining a signal indicating a height of a part of the user during movement;
processing the measurements of the acceleration to identify candidate movements corresponding to transitions between a standing posture and a sitting posture; and
determining an identified candidate movement as a transition from a sitting posture to a standing posture where the identified candidate movement coincides with an increase in the height in the signal and an identified candidate movement as a transition from a standing posture to a sitting posture where the identified candidate movement coincides with a decrease in the height in the signal.

13. An apparatus for identifying transitions between a standing posture and a sitting posture in measurements of the movement of a user, the apparatus comprising:
a hardware processor configured to:
process measurements of an acceleration experienced by the user to identify candidate movements corresponding to transitions between a standing posture and a sitting posture; and
determine an identified candidate movement as a transition from a sitting posture to a standing posture where the identified candidate movement coincides with an increase in a height in a signal indicating a height of a part of the user during movement, and determine an identified candidate movement as a transition from a standing posture to a sitting posture where the identified candidate movement coincides with a decrease in the height in the signal indicating the height of the part of the user.

14. The apparatus as claimed in claim 13 further comprising:
an accelerometer that measures an acceleration acting on the device in three dimensions, wherein the processing unit is configured to process the measurements of the acceleration from the accelerometer.

15. The apparatus as claimed in claim 13, further comprising:
a device that is configured to be worn by a user, the device comprising an accelerometer that measures an acceleration acting on the device in three-dimensions; and
a base unit that is configured to communicate with the device, wherein the processing unit is configured to process the measurements of the acceleration from the accelerometer.

* * * * *